(12) United States Patent
Ogata et al.

(10) Patent No.: US 7,211,790 B2
(45) Date of Patent: May 1, 2007

(54) MASS SPECTROMETER AND METHOD OF ANALYZING ISOMERS

(75) Inventors: Izumi Ogata, Ishioka (JP); Shinya Ito, Hitachinaka (JP); Shin-Ichiro Nishimura, Sapporo (JP); Kisaburo Deguchi, Sapporo (JP); Yasuhiro Takegawa, Sapporo (JP)

(73) Assignee: Hitachi High Technologies Corporation, Tokyo (JP)

( * ) Notice: Subject to any disclaimer, the term of this patent is extended or adjusted under 35 U.S.C. 154(b) by 0 days.

(21) Appl. No.: 11/132,174

(22) Filed: May 19, 2005

(65) Prior Publication Data

US 2005/0258355 A1     Nov. 24, 2005

(30) Foreign Application Priority Data

May 21, 2004   (JP)   ............................ 2004-151149

(51) Int. Cl.
*H01J 49/14*   (2006.01)
*G01N 30/02*   (2006.01)
*H01J 49/04*   (2006.01)

(52) U.S. Cl. ..................... 250/281; 250/282; 250/288

(58) Field of Classification Search ................ 250/288, 250/292, 281, 287
See application file for complete search history.

(56) References Cited

U.S. PATENT DOCUMENTS 5,493,115 A * 2/1996 Deinzer et al. ............. 250/281

| | | | |
|---|---|---|---|
| 6,624,408 B1 | 9/2003 | Franzen | |
| 6,677,114 B1 * | 1/2004 | Schneider et al. | 435/4 |
| 6,917,037 B2 * | 7/2005 | Ootake et al. | 250/282 |
| 7,049,581 B2 * | 5/2006 | Whitney et al. | 250/282 |
| 7,057,168 B2 * | 6/2006 | Miller et al. | 250/287 |
| 2002/0172961 A1 * | 11/2002 | Schneider et al. | 435/6 |
| 2005/0253061 A1 * | 11/2005 | Cameron et al. | 250/287 |

FOREIGN PATENT DOCUMENTS

| | | |
|---|---|---|
| JP | 8-124519 | 5/1996 |
| JP | 11-64285 | 3/1999 |
| JP | 2001-50945 | 2/2001 |
| JP | 2001-249114 | 9/2001 |

* cited by examiner

*Primary Examiner*—Nikita Wells
*Assistant Examiner*—Johnnie L Smith, II
(74) *Attorney, Agent, or Firm*—Mattingly, Stanger, Malur & Brundidge, P.C.

(57) ABSTRACT

The invention intends to determine a presence ratio between mixed compounds which are difficult to separate from each other by a separation unit and cannot be discriminated by MS. In a mass spectrometer with an MS$^n$ analysis function for ionizing a sample eluted from a separation unit for separating the sample into individual components, fragmenting an ion of a desired mass number, and performing a mass analysis of fragment ions, the mass spectrometer includes a database storing correlation information between an isomer presence ratio and a particular ion intensity ratio in a mass spectrum per isomer. An isomer ratio can be clarified even for a mixed sample of isomers, such as enantiomers, which are difficult to separate from each other by the separation unit and cannot be discriminated by MS.

7 Claims, 10 Drawing Sheets

MASS SPECTROMETER AND METHOD OF ANALYZING ISOMERS

BACKGROUND OF THE INVENTION

1. Field of the Invention

The present invention relates to a mass spectrometer, and more particularly to processing of mass spectrum data.

2. Description of the Related Art

As a method for identifying components of an unknown mixed sample, it has been widely practiced to connect any separation unit, e.g., a chromatograph, to a mass spectrometer, and to analyze a resulting mass spectrum by searching a database in which mass spectra of known compounds are stored beforehand. Methods of searching a mass spectrum database are disclosed in JP,A 11-64285 (Patent Reference 1), JP,A 2001-50945 (Patent Reference 2), JP,A 8-124519 (Patent Reference 3), JP,A 2001-249114 (Patent Reference 4), U.S. Pat. No. 6,624,408 (Patent Reference 5), etc.

A liquid chromatograph (LC) used as one of separation units is an apparatus for introducing an unknown mixed sample to a separation column to be adsorbed on a column surface, and feeding a mixture of plural solvents to the separation column while changing a mixing ratio of the solvents, thereby separating the sample into individual components based on a difference in reaction between each compound and the separation column. A combination of liquid chromatograph-mass spectrometer (LC/MS) is an apparatus for successively introducing the sample components separated by the LC to the mass spectrometer (MS) for detection of the components. When the sample components are successively introduced from the LC to the MS along with the solvents, each component is ionized by an ion source and produced compound ions are separated and detected depending on a mass-to-charge ratio (m/z). The detected result is accumulated for each retention time in the LC in the form of a chromatogram including the retention time and the mass spectrum.

The components in the mixed sample are represented as respective peaks in the chromatogram. By searching a mass spectrum database to find a mass spectrum having the same peaks, the structure of a compound represented by the peaks is identified. Also, the quantity of each component can be determined from a value of the peak area in the chromatogram.

SUMMARY OF THE INVENTION

To correctly identify and quantitatively measure the components of the mixed sample by the method of searching the mass spectrum database, it is important to isolate each of the components by the separation unit before the components are introduced to the MS.

However, when isomers are contained in the sample, in particular when the isomers are compounds, such as enantiomers, showing quite similar interactions with respect to the separation column, it is very difficult to separate those compounds from each other. If those compounds are subjected to mass analysis in a not-sufficiently separated state, a satisfactory result could not be obtained. More specifically, because of those compounds having the same mass number, even when a mass chromatogram is plotted based on the mass number of each compound, they cannot be discriminated from each other on the mass chromatogram. Stated another way, when the database search is used for identifying the sample components, isomers are impossible to discriminate them. In any of the above-cited Patent References, no considerations are paid to the database search regarding isomers.

Thus, when a sample contains enantiomers, a very long time has been required for reviewing separation conditions prior to the start of an analysis in the past. Also, a large amount of sample must have been consumed for the reason that, in reviewing the separation conditions, the state of separation is confirmed by measuring the sample while changing the conditions, and therefore the same sample requires to be measured several times.

Accordingly, it is an object of the present invention to provide a mass spectrometer and a method of analyzing isomers, both capable of determining a presence ratio between mixed compounds which are difficult to separate from each other by a separation unit and cannot be discriminated by MS.

To achieve the above object, the present invention provides a mass spectrometer with an $MS^n$ analysis function for ionizing a sample eluted from a separation unit for separating the sample into individual components, fragmenting an ion of a desired mass number, and performing a mass analysis of fragment ions, wherein the mass spectrometer includes a database storing correlation information between an isomer presence ratio and a particular ion intensity ratio in a mass spectrum per isomer.

The database stores characteristics newly found by the inventors. Even for a sample containing isomers having the same mass number, the isomer composition (presence ratio) can be determined by using that database.

According to the present invention, an isomer ratio can be clarified even for a mixed sample of isomers, such as enantiomers, which are difficult to separate from each other by the separation unit and cannot be discriminated by MS.

Also, since the isomer presence ratio can be determined with no need of isomer separation by the separation unit, it is possible to substantially cut the time required for reviewing the separation conditions and to save the amount of sample.

DESCRIPTION OF THE PREFERRED EMBODIMENTS

An embodiment of the present invention will be described below.

Figure 1A:
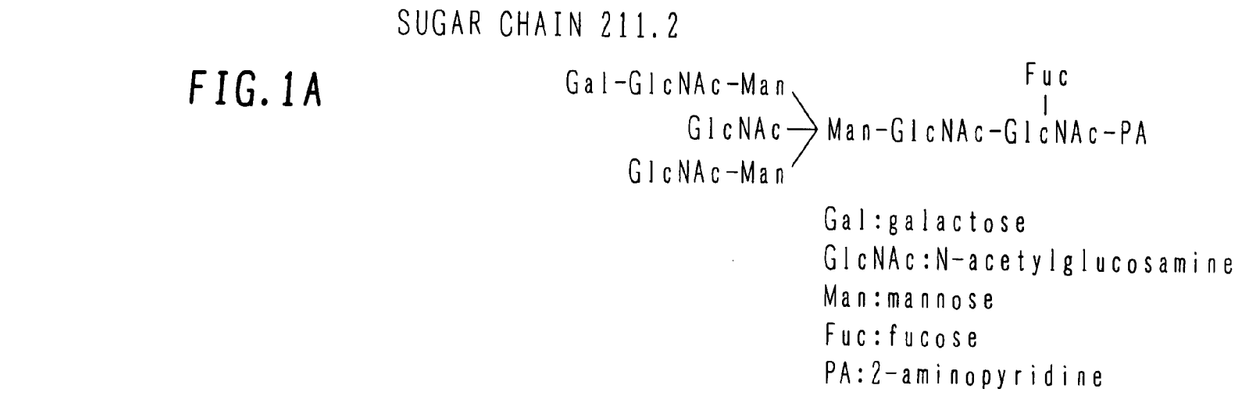
FIGS. 1A and 1B show the structures of components of a sample used in an embodiment of the present invention.
Figure 1B:
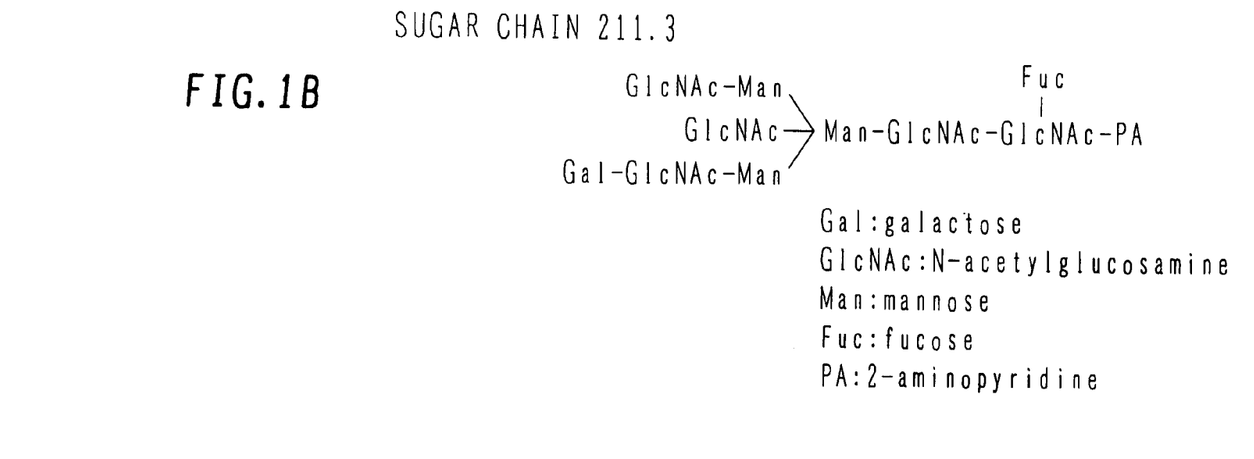

In this embodiment, a sugar chain sample is used as a sample as an analysis target. FIGS. 1A and 1B show the structures of sugar chains contained in the sample used in this embodiment. According to the nomenclature defined by Takahashi et al. in "Anal. Biochem.", 1988, No. 171, p. 73, those sugar chains are called 211.2 (in FIG. 1A) and 211.3 (in FIG. 1B), respectively. Because those sugar chains are enantiomers having different chains branched from mannose (Man) at the center, they have the same mass number. Therefore, ions detected from those sugar chains by an $MS^1$ analysis are only a pseudo-molecular ion of m/z 965 in common.

Figure 2:
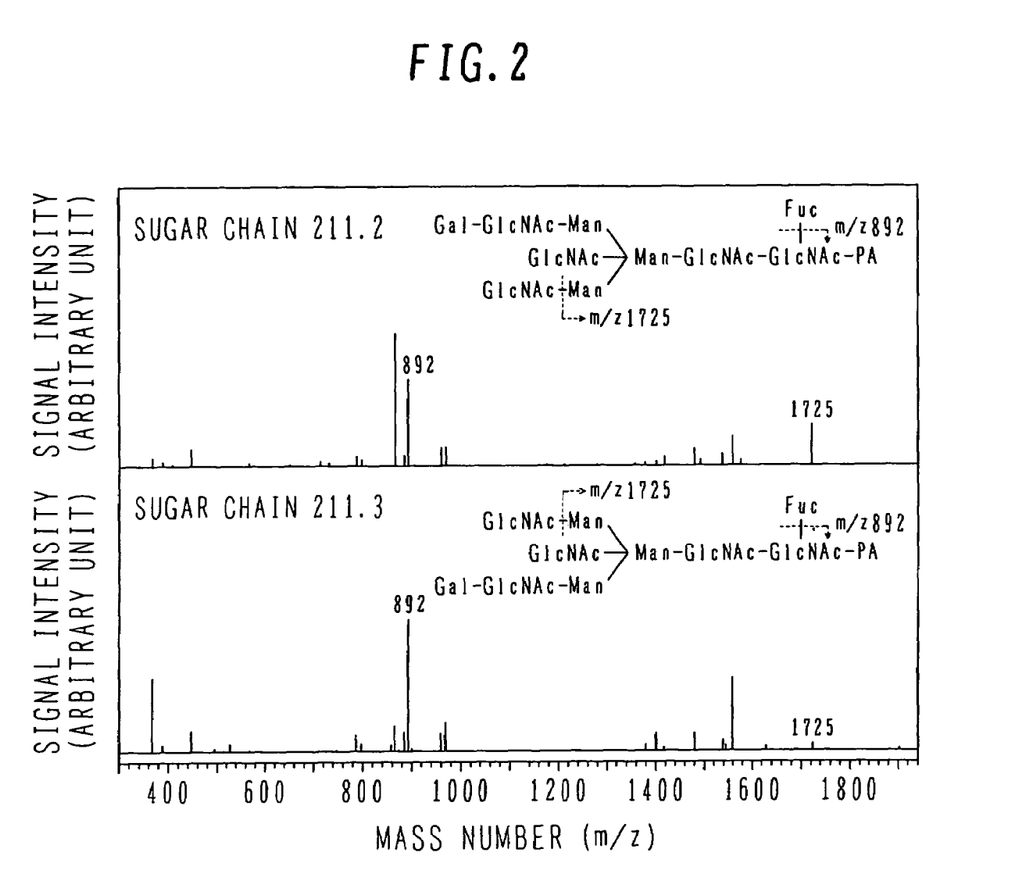
FIG. 2 is a chart showing mass spectra obtained with an $MS^2$ analysis of the sample used in an embodiment.

FIG. 2 shows the result of an $MS^2$ analysis made on the pseudo-molecular ion of m/z 965, as a parent ion, which has been obtained as the result of the $MS^1$ analysis made on each of the sugar chains. In each of the sugar chains 211.2 and 211.3, two fragment ions are detected, i.e., one of m/z 892 resulting from dissociation of Fuc at the end and the other of m/z 1725 resulting from dissociation of GlcNAc at one branched chain end from Man. The relative intensity of those two ions differs between the sugar chains 211.2 and 211.3. Fuc of m/z 892 is bonded to a portion common with both the sugar chain isomers, and therefore dissociation tendencies of Fuc are substantially equal between the sugar chains 211.2 and 211.3. On the other hand, GlcNAc of m/z 1725 is bonded to the branched chain in which the structures of the sugar chain isomers differ from each other, and therefore dissociation tendencies of GlcNAc are different between the sugar chains 211.2 and 211.3. Thus, the inventors found that a fragment ion, such as m/z 1725, related to a portion in which the structures of sugar chain isomers differ from each other is detected with the intensity specific to each isomer.

Figure 3:
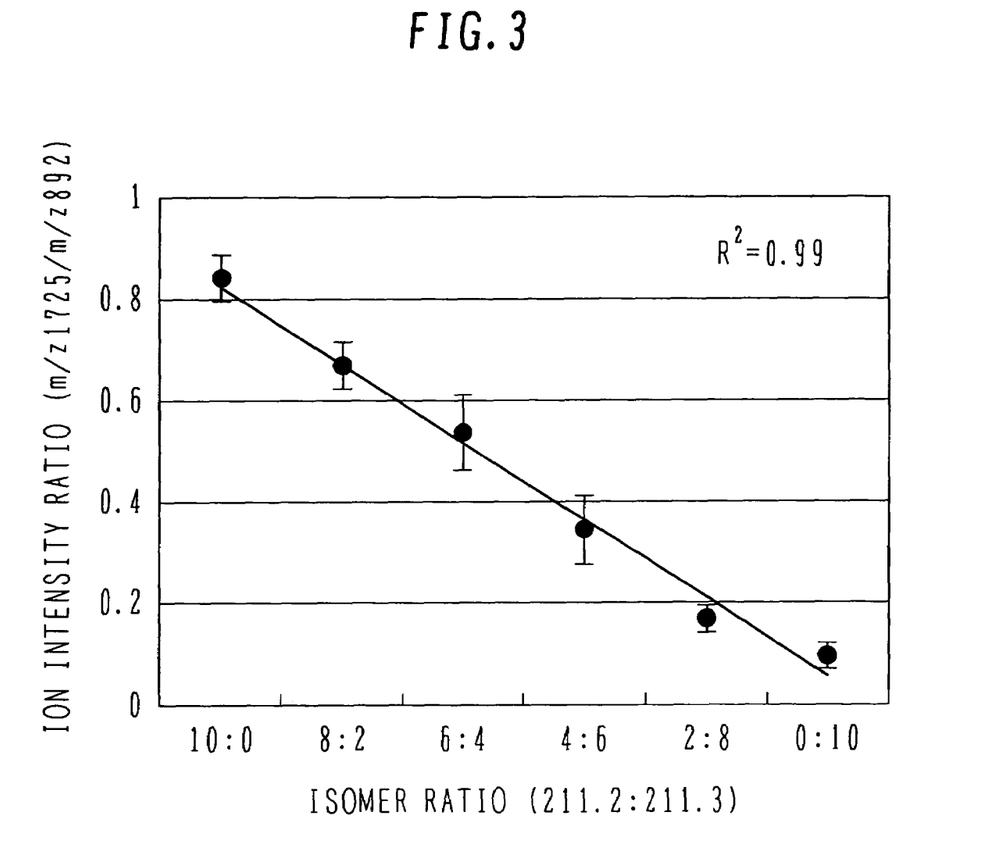
FIG. 3 is a graph showing the correlation between an isomer ratio of the sample used in the embodiment and an intensity ratio between particular ions within the mass spectra.

Further, the inventors made studies on the $MS^2$ analysis results of mixed samples of 211.2 and 211.3 containing the sugar chain isomers at various ratios to examine values of the ion intensity of m/z 1725 normalized based on the ion intensity of m/z 892. Then, the inventors found that there is linear correlation between the ion intensity ratio and the isomer ratio as shown in FIG. 3.

Figure 4A:
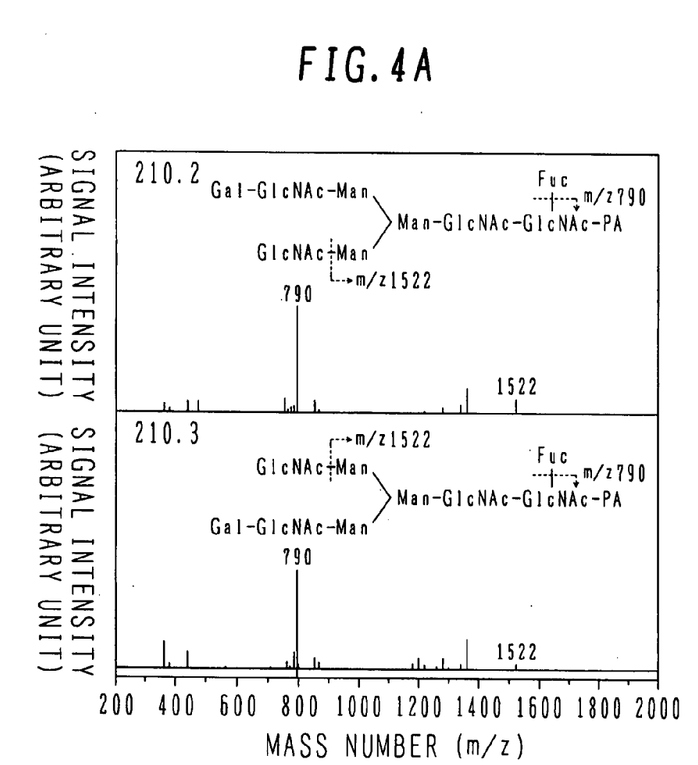
FIGS. 4A and 4b are a chart showing mass spectra obtained with an $MS^2$ analysis of sugar chains 210.2, 210.3 and a graph showing the correlation between an isomer ratio and an intensity ratio between particular ions within the mass spectra.
Figure 4B:
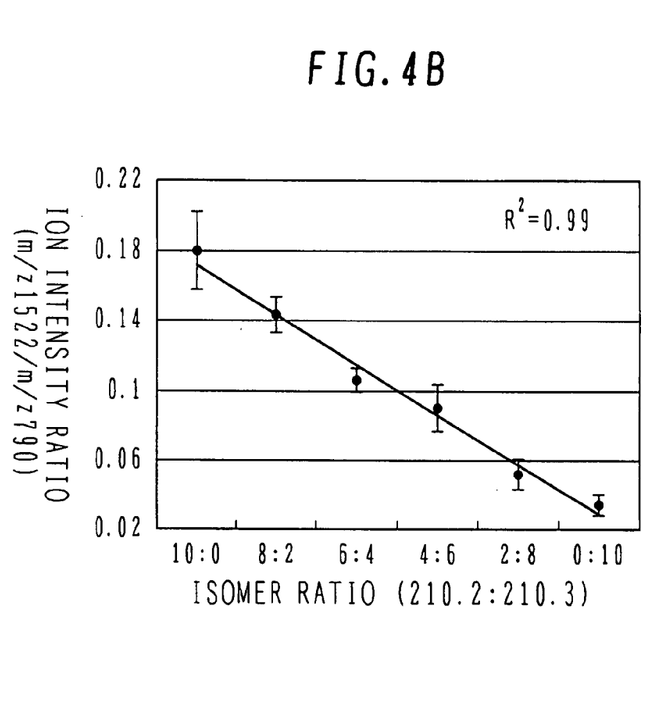
Figure 5A:
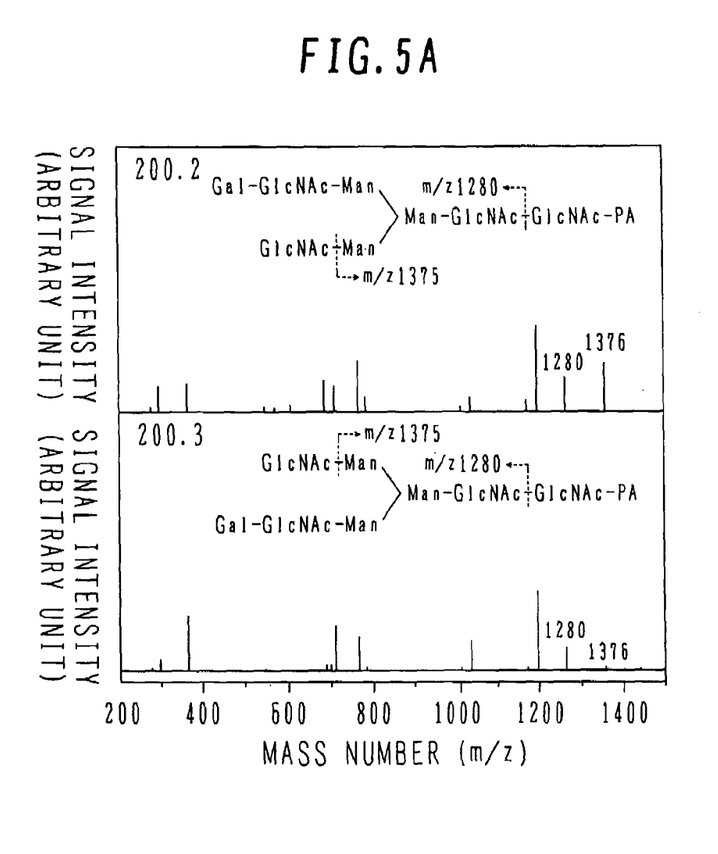
FIGS. 5A and 5B are a chart showing mass spectra obtained with an $MS^2$ analysis of sugar chains 200.2, 200.3 and a graph showing the correlation between an isomer ratio and an intensity ratio between particular ions within the mass spectra.
Figure 5B:
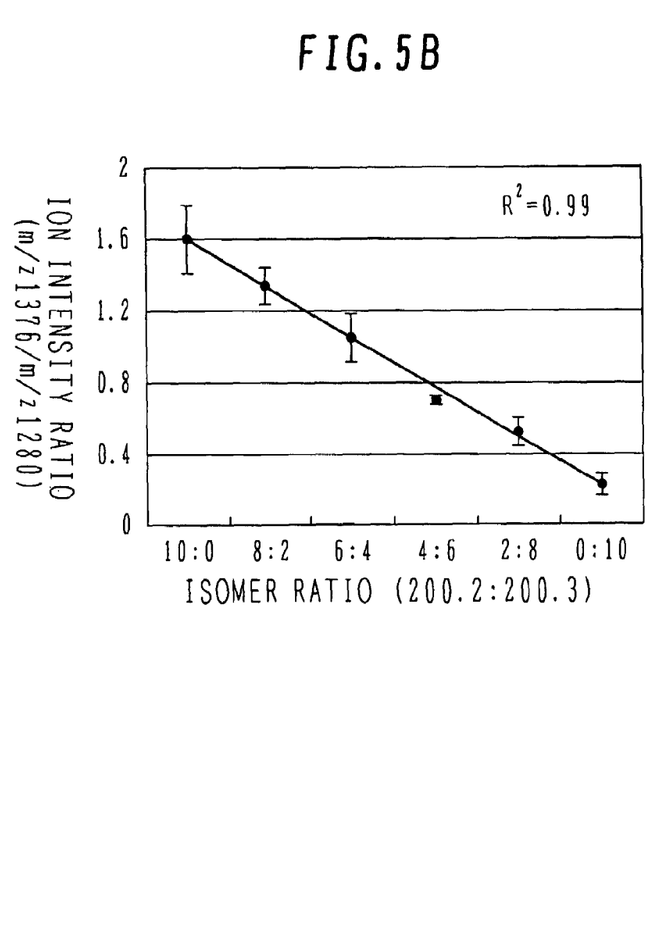

Such linear correlation was also confirmed for other types of sugar chain isomers. For isomers of sugar chains 210.2 and 210.3, as shown in FIGS. 4A and 4B, linear correlation was found between a ratio of m/z 790 to m/z 1522 and an isomer ratio. Further, for isomers of sugar chains 00.2 and 200.3, as shown in FIGS. 5A and 5B, linear correlation was found between a ratio of m/z 1280 to m/z 1376 and an isomer ratio.

Figure 6:
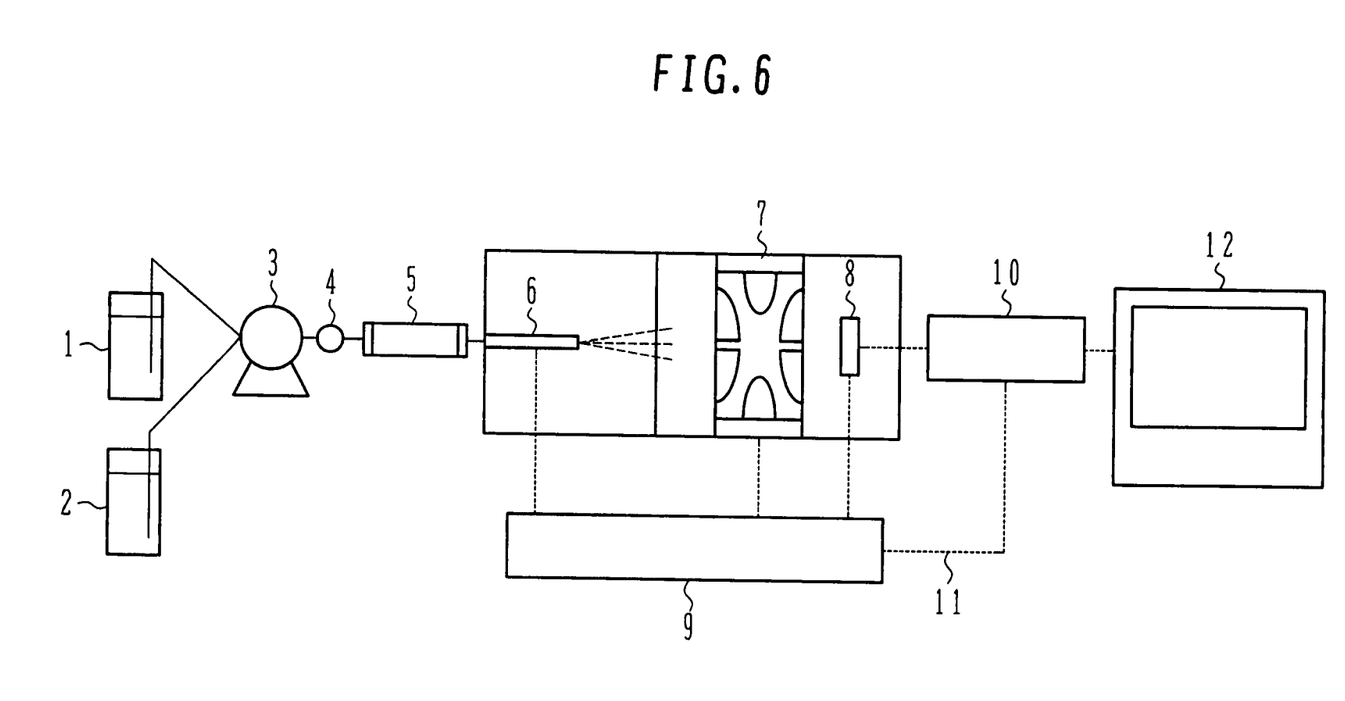
FIG. 6 is a schematic view showing the configuration of LC/MS according to the embodiment.

By utilizing that linear correlation, even when isomers in a state of being not sufficiently separated from each other by LC, for example, are introduced to MS, the composition ratio between the isomers can be determined from a resulting mass spectrum. FIG. 6 shows the configuration of a mass spectrometer (MS) used in this embodiment. This embodiment represents the case using a combination of liquid chromatograph-mass spectrometer (LC/MS) in which the LC is connected as one example of a separation unit to the MS. Instead of the LC, however, the separation unit may be of any other suitable type (e.g., a gas chromatograph) so long as it is able to separate a sample into individual components.

The LC/MS used in this embodiment comprises a pump 3 with the function of selectively mixing a plurality of solvents 1, 2 with each other and feeding a solvent mixture while changing the composition of the mixture with time, a sample injector 4 for introducing a sample into a flow passage, a column 5 for separating the sample into individual components, an ion source 6 for ionizing the sample which has been separated into the components by the column 5, a mass separation section 7 of ion trap type capable of separating produced ions in terms of mass and performing an $MS^n$ analysis, a detector 8 for detecting the ions separated in terms of mass, a controller 9 for controlling the above-mentioned pieces of equipment, a data processing unit 10, signal lines 11 for interconnecting the above-mentioned pieces of equipment, and a display unit 12 for displaying the measured data and the search results.

The sample injected from the injector 4 to the flow passage is separated into individual components by the column 5 and then introduced to the ion source 6. Sample ions ionized by the ion source 6 are introduced to the mass separation section 7. In the mass separation section 7, the sample ions are separated from each other in terms of mass. Then, according to setting made by an operator, the ion having the desired mass number is fragmented and subjected to a mass analysis, i.e., successive steps of $MS^n$ (n=2, 3, 4, . . . ). The ions having been separated in terms of mass are introduced to the detector 8 and are detected as a mass spectrum. The mass spectrum is sent to the data processing unit 10 via the signal line 11 and is processed for display on the display unit 12. Note that the mass separation section 7 used in this embodiment is of the ion trap type, but any other suitable type can also be used so long as it is able to perform the $MS^n$ analysis.

Figure 10:
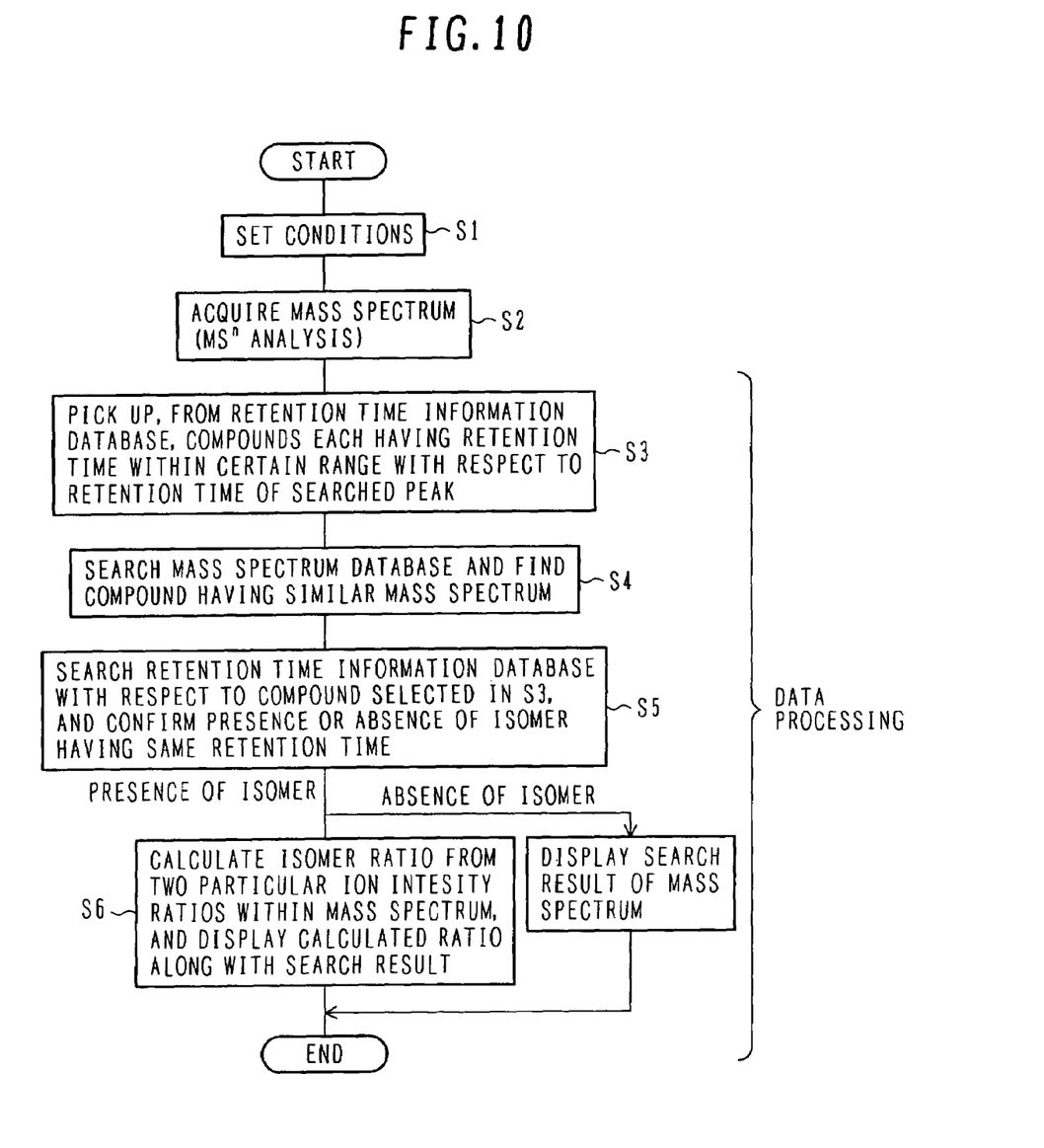
FIG. 10 is a flowchart showing one example of an analysis sequence according to the embodiment.

One example of an analysis sequence with the above-described LC/MS will be described below. FIG. 10 is a flowchart showing one example of the analysis sequence, and the following description is made with reference to the flowchart.

Condition setting of the LC/MS (e.g., setting of an exponent of the $MS^n$ analysis) is first made, and the analysis is then preformed in accordance with the setting to acquire a mass spectrum of a sample (S1 and S2). In this embodiment, it is assumed that a sugar chain mixture cut from human immunoglobulin, i.e., glycoprotein, is used as an analysis target and the analysis is performed until $MS^2$.

Figure 7:
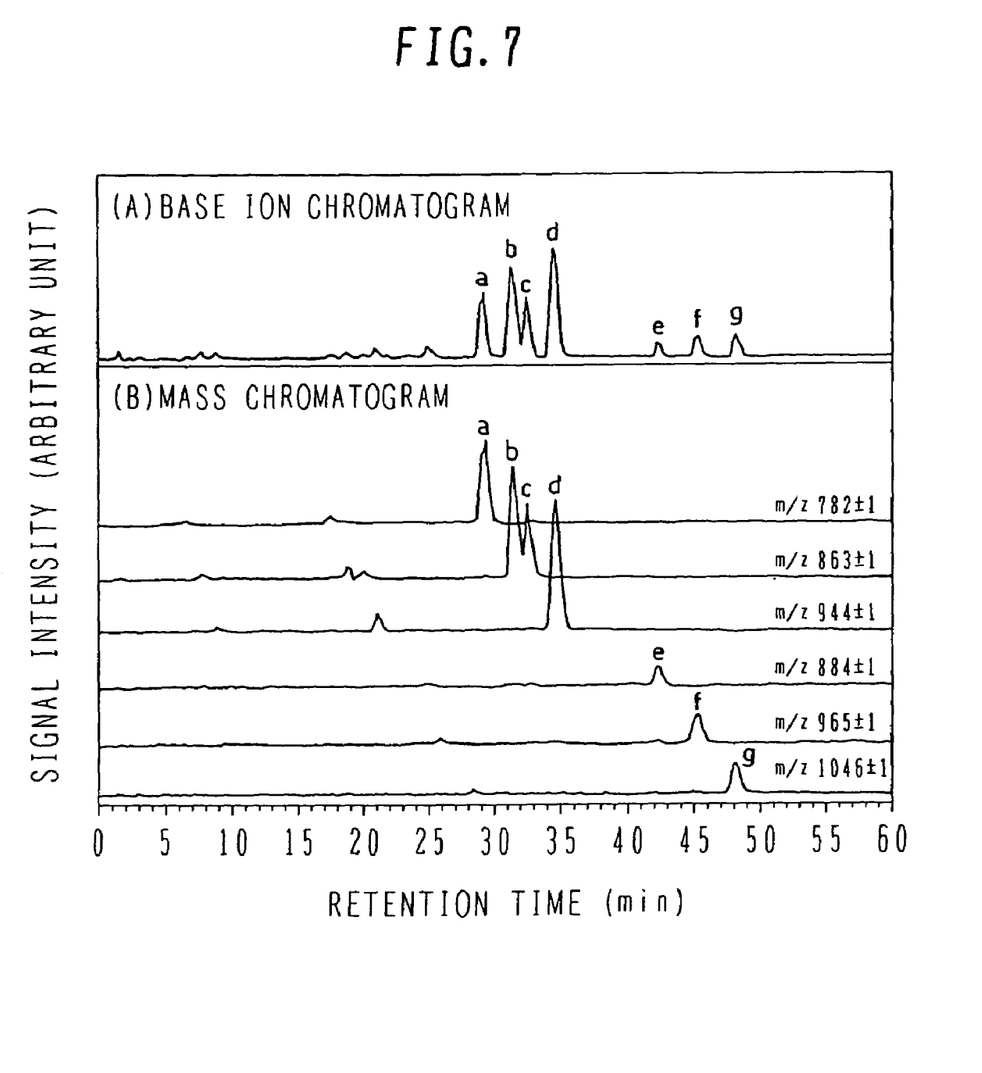
FIG. 7 is a chart showing the result of an LC/MS analysis of human immunoglobulin.

FIG. 7 shows a base ion chromatogram obtained by analyzing the sample with the LC/MS and a mass chromatogram including peaks. Individual components of the sample are separated from each other by the LC column 5, and peaks a-g shown in (A) of FIG. 7 are detected.

The sugar chain mixture contains the above-mentioned two kinds of sugar chains 211.2 and 211.3 as well. However, it is difficult to separate those sugar chains from each other by the LC column 5, and they are detected together as the mixture of the two kinds of sugar chains as represented by the single peak f in FIG. 7. Also, because those sugar chains have the same mass number, it is also impossible to discriminate them from each other on the mass chromatogram.

Figure 8:
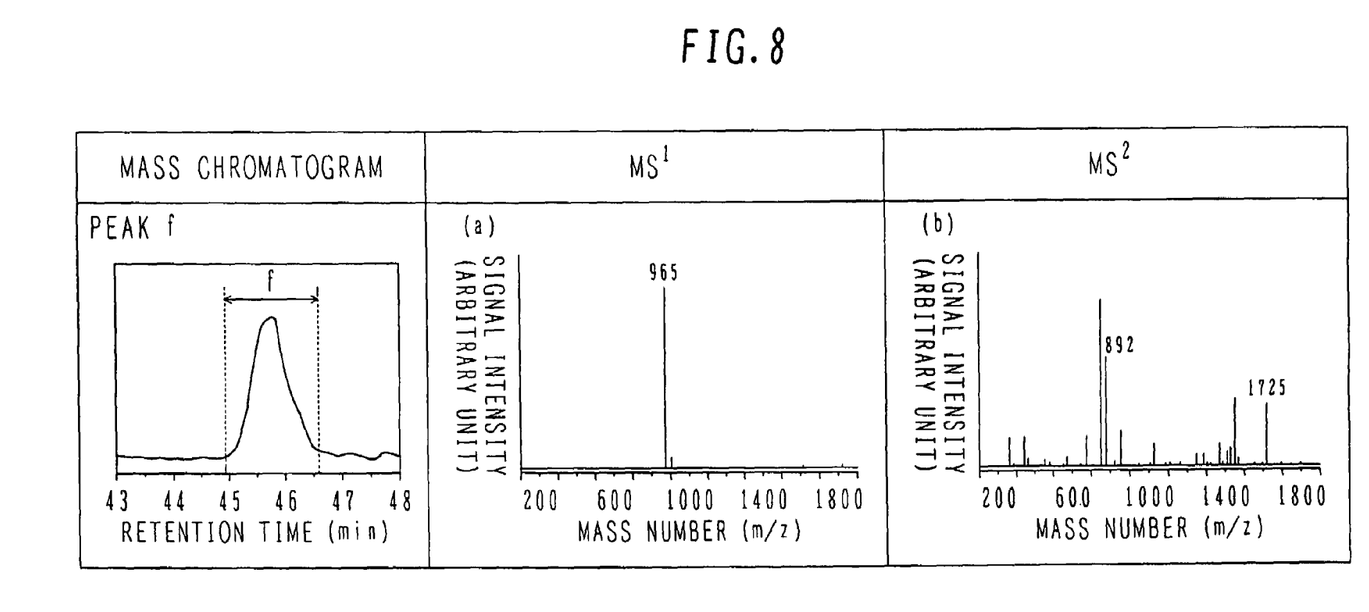
FIG. 8 is a chart showing a mass chromatogram and mass spectra of peak f.

FIG. 8 shows $MS^1$ and $MS^2$ spectra of the peak f. As shown, the pseudo-molecular ion of m/z 965 was detected in the $MS^1$ spectrum. Then, a Fuc fragment ion of m/z 892 and a GlcNAc fragment ion of m/z 1725 were detected in the $MS^2$ spectrum by using the pseudo-molecular ion of m/z 965 as a parent ion.

The data processing unit 10 of this embodiment stores therein a database that stores standard $MS^2$ spectra of various compounds, a database that stores standard chromatogram retention time information (GU indexes) of various compounds, and a database that stores the correlation information between the isomer composition (presence ratio) and the particular ion intensity ratio in the mass spectrum per isomer.

Figure 9:
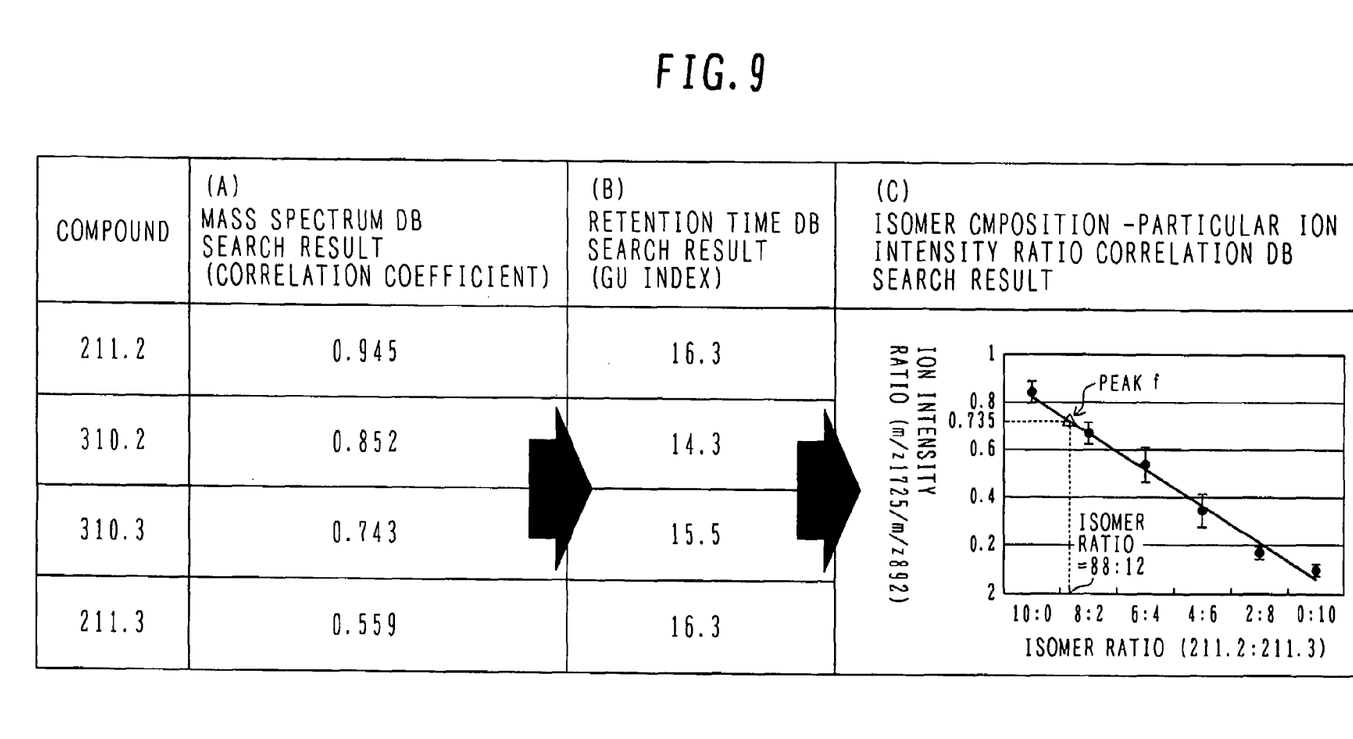
FIG. 9 shows the result of a database search according to the embodiment.

Based on the retention time of each detected peak, the data processing unit 10 picks up, from the chromatogram retention time information database, compounds each having the retention time within a certain range with respect to the retention time of each detected peak (S3). Here, "compounds each having the retention time within a certain range" mean all of the compounds each having the retention time within a range, which was set by the operator beforehand in consideration of an allowable error, with respect to the retention time of each peak. As the search result with respect to the peak f containing isomers, sugar chains 211.2, 310.2, 310.3, 211.3, etc., indicated in column "Compound" of FIG. 9, were picked up as the compounds falling within the retention time range set for the peak f.

Then, the mass spectra of the picked-up compounds are compared with the $MS^2$ spectrum for each peak, thereby to find a compound having similarity in mass spectrum (S4). More specifically, the $MS^2$ spectra of the compounds picked up in S3 are read out of the database storing the various standard $MS^2$ spectra and are compared with the $MS^2$ spectrum for each peak, thereby calculating similarity per compound. The similarity is represented by a correlation coefficient or a sine coefficient. This embodiment employs the correlation coefficient. As a result of the calculation, as shown in (A) of FIG. 9, a high correlation coefficient of 0.945 was obtained between the $MS^2$ spectrum of the peak f and the spectrum of the sugar chain 211.2. As the other search results, the correlation coefficients of 0.852 and 0.743 were obtained for the sugar chains 310.2 and 310.3, respectively. On the other hand, the isomer 211.3 included in the peak f together with 211.2 showed a low correlation coefficient of 0.559. Thus, according to the comparison of the mass spectrum, a probability of 211.3 being contained in the sample was low.

Subsequently, the data processing unit 10 searches the retention time information database with respect to each of the picked-up compounds (S5). This search shows, as indicated in (B) of FIG. 9, the presence of the isomer 211.3 that belongs to the peak f and has the same GU index as 211.2 for which the result of the mass spectrum search showed the highest correlation coefficient. Thus, it is understood that 211.2 and 211.3 are eluted at the same time in the chromatography, and there is a probability of those two kinds of sugar chains being contained in the peak f in a mixed way. It is also understood that those two kinds of sugar chains are isomers and hence cannot be discriminated from each other on the mass chromatogram. For the other peaks containing no isomers, because compounds having the same GU index are not present, the absence of an isomer is determined and the result of the mass spectrum search is displayed on the display unit 12. The processing is thereby brought to an end.

If there is a compound having the same GU index, the data processing unit 10 further determines a presence ratio between the relevant isomers. For the two kinds of retrieved sugar chain isomers 211.2 and 211.3, as shown in (C) of FIG. 9, a search is performed on the database storing the correlation information between the sugar chain isomer composition (presence ratio) and the particular ion intensity ratio in the mass spectrum (S6). The correlation coefficient database stores, corresponding to each combination of two kinds of isomers for which the composition is to be determined, two kinds of ions for which an intensity ratio is to be determined and the correlation between the ion intensity ratio and the isomer composition (presence ratio) per compound. As a result of calculating the intensity ratio of the two kinds of ions (m/z 1725 and m/z 892), which were determined with search regarding 211.2 and 211.3, based on the result of the $MS^2$ analysis, the intensity ratio between those two ions was 0.735. Then, by determining the isomer composition from that value of the intensity ratio, the isomer ratio of 211.2: 211.3=88:12 was obtained.

Finally, the determined isomer ratio is displayed on the display unit 12 along with the search result of the mass spectrum database. The processing is thereby brought to an end.

According to this embodiment, as described above, because of including the various databases mentioned above, it is possible to detect isomers which are not separated from each other by the LC, an to determine the presence ratio between those isomers.

What is claimed is:

1. A mass spectrometer with an $MS_n$ analysis function for ionizing a sample eluted from a column for separating the sample into individual components, fragmenting an ion of a desired mass number, and performing a mass analysis of fragment ions, said mass spectrometer comprising:
   a first database storing retention time information for each of a plurality of compounds; and
   a second database storing correlation information between an ion intensity ratio of fragment ions of a mixture of isomers and an isomer presence ratio of said isomers in said mixture per isomer,
   wherein said databases are used to determine whether the samples contains isomers, and to calculate the presence ratio between the isomers if the samples contains the isomers.

2. The mass spectrometer according to claim 1, wherein said column is a liquid chromatograph.

3. The mass spectrometer according to claim 1, wherein the presence of isomers in the sample is determined when the presence of compounds having the same retention time is confirmed based on said first database, and the isomer presence ratio is calculated based on said second database.

4. The mass spectrometer according to claim 1, wherein said mass spectrometer further includes a third database storing $MS^2$ spectra of the plurality of compounds.

5. A method of analyzing isomers by using a column for separating a sample into individuals components and a mass spectrometer with an $MS^n$ analysis function for fragmenting an ion of a desired mass number and performing a mass analysis of fragment ions, said mass spectrometer including a first database storing retention time information for each of a plurality of compounds, a second database storing correlation information between an ion intensity ratio of fragment ions of a mixture of isomers and an isomer presence ratio of said isomers in said mixture per isomer, and a third database storing $MS^2$ spectra of the plurality of compounds, said method comprising the steps of:
   obtaining a mass spectrum with an $MS^2$ analysis of the sample;

searching said third database based on the obtained mass spectrum, and computing similarity between the obtained mass spectrum and each of the compounds in said third database;

searching said first database to check the retention time of each of the compounds for which similarity has been computed, and finding the compounds having the same retention time; and determining the compounds having the same retention time to be isomers, and computing an isomer presence ratio based on the obtained mass spectrum by using said second database.

6. The method of analyzing isomers according to claim 5, further comprising the step of, before calculating the similarity, selecting compound candidates, for each of which similarity is to be computed, from said first database based on the retention time at which the mass spectrum has been obtained with the $MS^2$ analysis.

7. A mass spectrometer with an $MS^n$ analysis function for ionizing a sample eluted from a column for separating the sample into individual components, fragmenting an ion of a desired mass number, and performing a mass analysis of fragment ions, said mass spectrometer comprising:

a database storing correlation information between an ion intensity ratio of fragment ions of a mixture of isomers and an isomer presence ratio of said isomers in said mixture per isomer.

* * * * *